United States Patent [19]

Floyd

[11] Patent Number: 5,685,831
[45] Date of Patent: Nov. 11, 1997

[54] POSTULATOR

[76] Inventor: John P. Floyd, 137 Margaret St., Mobile, Ala. 36607

[21] Appl. No.: 674,627

[22] Filed: Jul. 5, 1996

[51] Int. Cl.⁶ ..................................... A61F 5/00
[52] U.S. Cl. .................. 602/19; 602/17; 602/18; 2/45
[58] Field of Search ............. 602/17–19; 2/44, 2/45; 128/869, 870

[56] References Cited

U.S. PATENT DOCUMENTS

| | | | |
|---|---|---|---|
| 443,764 | 12/1890 | Hilliard | 602/19 |
| 637,156 | 11/1899 | Potts | 2/44 |
| 796,623 | 8/1905 | Bailey | 2/45 |
| 836,802 | 11/1906 | Daniel | 2/44 |
| 1,316,915 | 9/1919 | Meyer et al. | 602/19 |
| 1,371,690 | 3/1921 | Kelly | 2/44 |
| 1,650,650 | 11/1927 | Pieper | 602/19 |
| 1,755,641 | 4/1930 | Foulke | 602/19 |
| 2,973,030 | 2/1961 | Matthewson | 2/44 X |
| 4,173,973 | 11/1979 | Hendricks | 602/19 |
| 4,541,419 | 9/1985 | Osawa | 602/19 |
| 4,640,269 | 2/1987 | Goins | 602/19 |
| 4,829,989 | 5/1989 | Deamer et al. | |
| 5,135,471 | 8/1992 | Houswerth | |
| 5,199,940 | 4/1993 | Morris et al. | 602/19 |

*Primary Examiner*—Linda C. Dvorak
*Attorney, Agent, or Firm*—Patent & Trademark Services; Joseph H. McGlynn; Thomas Zack

[57] ABSTRACT

A back brace having interlocking frame members jointed at a first pivotal hinge connection where the two vertically disposed members join the other member. The two vertical members join each other at an adjustable second hinged connection. Above the first hinge connection the upper vertical member may be removed to make the brace appear less conspicuous. Four straps with end hook and loop members allow attachment of the brace to a user's forehead, shoulders and waist.

6 Claims, 1 Drawing Sheet

POSTULATOR

BACKGROUND OF THE INVENTION

This invention relates to a back brace used to improve a user's posture. Many back braces act as spine immobilizing and posture improving devices. None, however, utilize the unique combination of a "T" shaped frame having a pivoting cross point combined with a hinged vertical member as disclosed in this invention.

DESCRIPTION OF THE PRIOR ART

Braces which are strapped to a user's back or other body members are well known in the art. For example, in the U.S. Pat. No. 4,640,269 to Goins a brace has a strap with a widened middle portion for a pad. The Deamers invention (U.S. Pat. No. 4,829,989) discloses a U shaped support with a strap and an adjustable spring biased hinge. Both the user's chest and thighs are contacted by pads to provide support for the back when performing so called stoop labor. The Housewerth invention (U.S. Pat. No. 5,135,471) uses a strap with a cruciform anterior spinal hyperextension orthosis with a rigid cruciform base. Several user frontal portions are engaged by pads two of which are located on attached by a pivotal connected to the upper end of an upright. Still another brace is disclosed in the Morris U.S. Pat. No. 5,199,940 wherein a rod is held firmly to a wearer's spine by several adjustable elastic belts around the abdominal, shoulder, and head areas. None, however, disclose a back brace having the unique combination of a T shaped support frame with a pivoting cross point and a hinged vertical member as disclosed herein.

SUMMARY OF THE INVENTION

The back brace has a "T" shaped design made from three interconnected frame members. At the cross point joining the vertical to the horizontal members is a hinge joint to permit free shoulder movement. Further down the vertical members is a second hinge with an adjustable band tensioner. Above the cross point is a removable vertical member. Padding may cover the frame and straps are available to attach the brace to a user's forehead, shoulders and waist. For attachment, loop and hook fasteners may be used at or near the straps' ends.

DESCRIPTION OF THE PREFERRED EMBODIMENT

Figure 1:
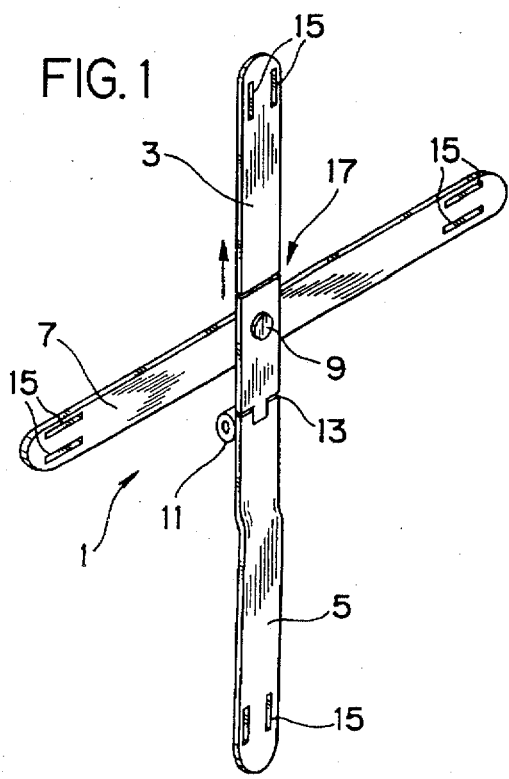
FIG. 1 shows the preferred embodiment for the brace's frame support.

As shown in FIG. 1 the support frame 1 has three interlocking injection molded ABS plastic members-the two joined vertical members 3 and 5 and the horizontally disposed member 7. At the cross point 9 the horizontal and vertical members are pivotally joined to form a "T" shaped frame structure. The lower vertical member 5 extends above the cross point and has a tensioner adjustment assembly 11 below the cross point. This assembly permits adjustment of tension at the vertical hinge 13 in the lower member 5. Near the free ends of each frame support member are two parallel strap receiving slots 15. Slightly above the cross point is a horizontal break point 17 where the upper vertical member 3 is joined to the lower vertical member 5 and at which the upper member can be removed.

Figure 2:
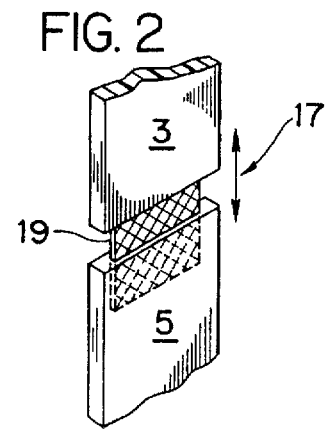
FIG. 2 is an enlarged detail view of the FIG. 1 frame's removable connection for the upper vertical member.

FIG. 2 shows an enlarged detail view of the FIG. 1 frame's removable connection at break point 17 as the upper member is being separated from the upper vertical member 5. Similar to a mortise and tenon joint, there is a projecting member 19 (tenon) in the upper member which fits into a cavity (mortise) in the lower member 5. By holding one member and pulling the other the upper member 3 can be removed to make wearing the brace less conspicuous in public.

Figure 3:
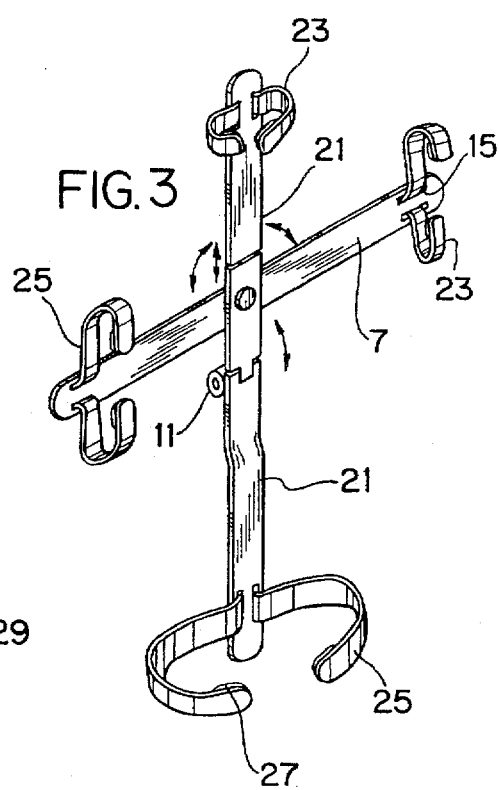
FIG. 3 depicts the complete support frame with strap attachments and covering.

FIG. 3 depicts the complete support frame with strap attachments and covering. The covering consists of padded strips 21 which are attached to the vertical members where they engage a user's body. The four soft nylon webbing straps 23 are covered by a self stick polyurethane foam rubber 25 and fit through the members' slots 15. Each strap is sized such that two fit around the user's shoulders and both the user's forehead and waist each have one. At each strap's free end there are loop and hook (VELCRO)™ fasteners 27 to hold the brace to the user and accommodate a great variety of different users.

Figures 4, 5:
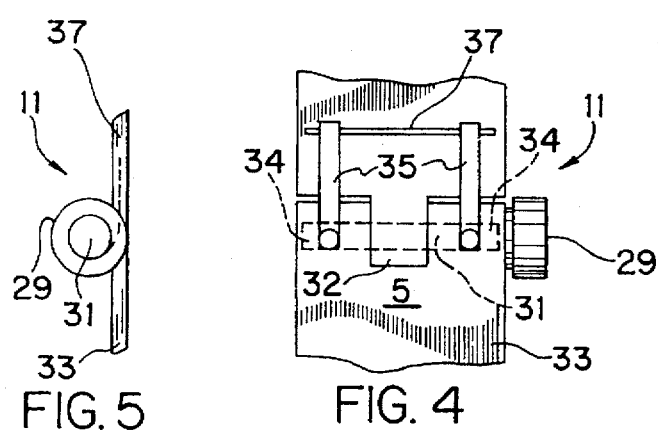
FIG. 4 shows a front view of the tension hinge adjustment assembly.
FIG. 5 is a side view of the FIG. 4 assembly.

FIGS. 4–5 show the adjustable tensioner assembly 11 in greater detail. When knob 29 is turned by a user the attached internal shaft 31 rotates. This shaft extends through a hole in an extending tongue 32 in the upper attachment attachment 33. At its ends the shaft is held by two shaft receiving end pockets 34.

In this way the shaft acts a hinge connection which can freely rotate. Two separate rubber tension bands 35 are fixed to the shaft at one end and fixed to the upper hinge attachment 37 at their other end. When the shaft is rotate either tension or relaxation is imparted to the rubber bands. Since the bands span the hinge connection break point 13, applying more tension to them would make moving the hinge more difficult.

In use a user would wear the invention over clothing during convenient moments of the day. The frame's rigid structure would assist the user in strengthening his muscles and ligaments and adjust his spine for a better posture. The adjustable center hinge (see FIG. 4–5) can be tightened or loosened depending on the user's posture requirements. Because this brace is significantly less bulky and heavy than conventional braces, it could also help and aid users with mild cases of scoliosis and other back related aches and injuries.

The primary support plastic frame members would best be manufactured of lightweight but strong ABS plastic using the injection molding process. Injection molding is a plastic molding process whereby heat softened plastic material is forced under very high pressure into a metal cavity mold, usually aluminum or steel, which is relatively cool. The inside cavity of the mold is comprised of two or more halves, and is the same desired shape as the product to be formed (in this case the support frame). High pressure hydraulics are used to keep the mold components together during the actual injection phase of the molding process. The injected plastic is allowed to cool and harden in the mold. The hydraulics holding the multiple component mold cavity together are released, the mold halves are separated and the solid formed plastic item is removed. Injection molding can be highly automated process and is capable of producing extremely detailed parts at a very cost effective price. The process should be invaluable in producing this invention's brace frame cost effectively.

The four nylon webbing straps covered with a self-stick foam padding material can have their hoop and loop fasteners sewn or ultrasonically welded to them. All of the strap components are available "off the shelf" items.

Although the Postulator and the method of using the same according to the present invention has been described in the foregoing specification with considerable details, it is to be understood that modifications may be made to the invention which do not exceed the scope of the appended claims and modified forms of the present invention done by others skilled in the art to which the invention pertains will be considered infringements of this invention when those modified forms fall within the claimed scope of this invention.

What I claim as my invention is:

1. A back brace comprising:

three interconnected brace frame members two of which members are generally vertically disposed, one of said two vertically disposed members joining the other interconnected frame member at a first hinge joint such that the other member's ends may move up and down with respect this vertically disposed member;

a second tension adjustable hinge joint joining said two vertically disposed members to each other; and strap attachment means for attaching the three interconnected frame members to a user's forehead, shoulders and waist.

2. The invention as claimed in claim 1, wherein the upper one of said two vertically disposed members can be removed above the hinge joint from said other vertically disposed member.

3. The invention as claimed in claim 2, wherein said tension adjustable hinge joint includes an adjustable knob which can impart tension to tensioning members spanning the joint between the two vertical members.

4. The invention as claimed in claim 3, wherein strap attachment means includes hook and loop fasteners near their ends.

5. The invention as claimed in claim 4, wherein there is a mortise and tenon connection between two sections of the upper of said two vertically disposed frame members.

6. The invention as claimed in claim 5, including a padded covering for at least some of said frame members to protect a user.

* * * * *